United States Patent [19]

Kline

[11] 4,367,759

[45] Jan. 11, 1983

[54] FLEXIBLE TEETH-CLEANING DEVICE

[76] Inventor: Larry H. Kline, 18 Broad St., Suite 805, Charleston, S.C. 29401

[21] Appl. No.: 351,271

[22] Filed: Feb. 22, 1982

[51] Int. Cl.³ .............................................. A61C 15/00
[52] U.S. Cl. .......................................... 132/89; 132/93
[58] Field of Search ............................. 132/89, 90, 93

[56] References Cited

U.S. PATENT DOCUMENTS

| | | | |
|---|---|---|---|
| 3,078,856 | 2/1963 | Bender et al. | 132/93 |
| 3,646,628 | 3/1972 | Halford | 132/93 |
| 3,892,040 | 7/1975 | Marquis . | |
| 3,892,249 | 7/1975 | Jones et al. . | |
| 3,896,824 | 7/1975 | Thornton . | |
| 3,964,122 | 6/1976 | Kurdy . | |

Primary Examiner—Richard J. Apley
Assistant Examiner—Sherri Vinyard
Attorney, Agent, or Firm—Larry Harold Kline

[57] ABSTRACT

A device is disclosed for cleaning teeth and adjacent areas comprising a shaft with a cleaning end, a flexible rest with an opening through which the shaft extends which is operative to be pressed against the teeth and adjacent areas to stabilize the position of the device, and a securing apparatus secured to the shaft and to the flexible rest.

8 Claims, 21 Drawing Figures

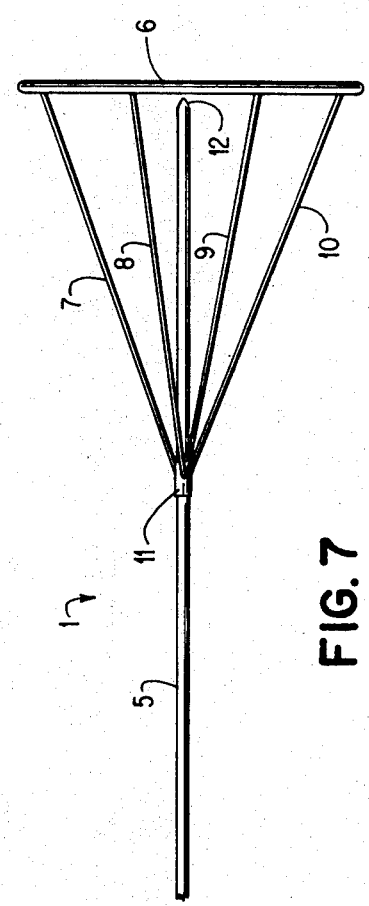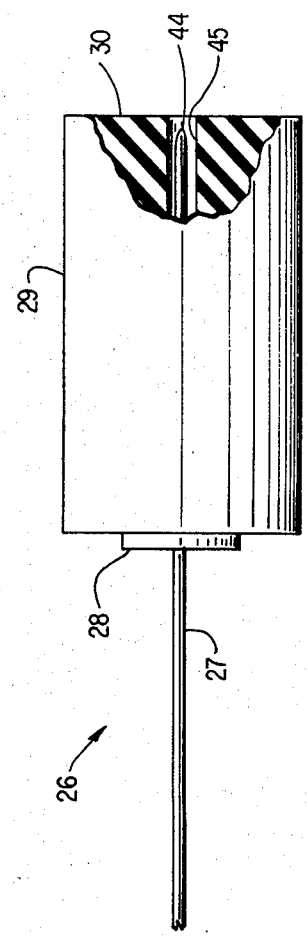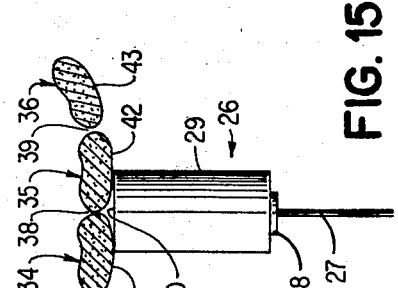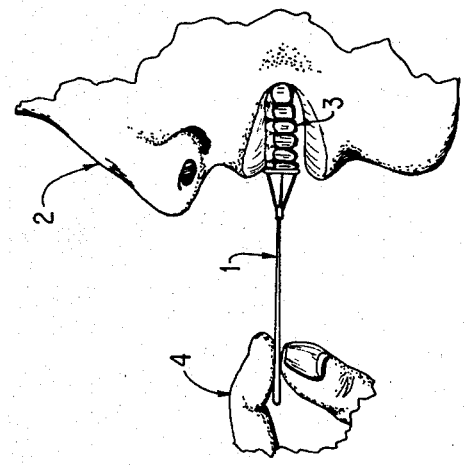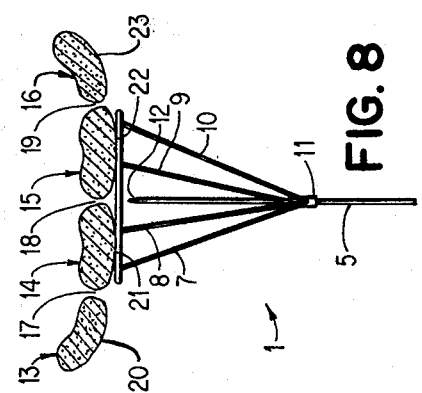

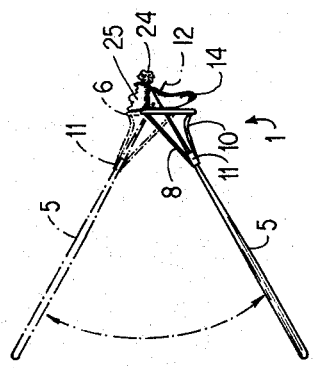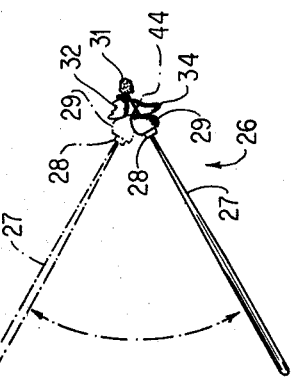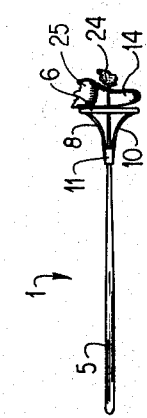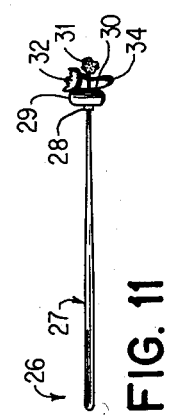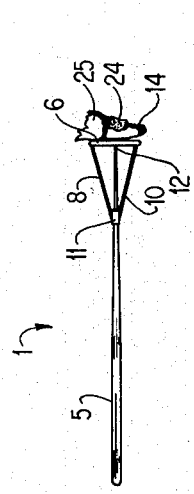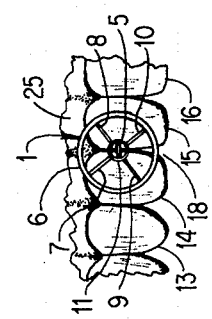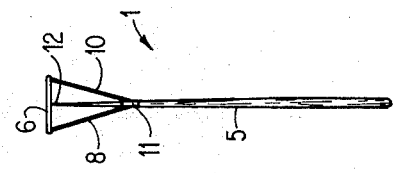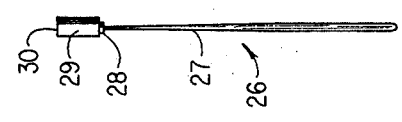

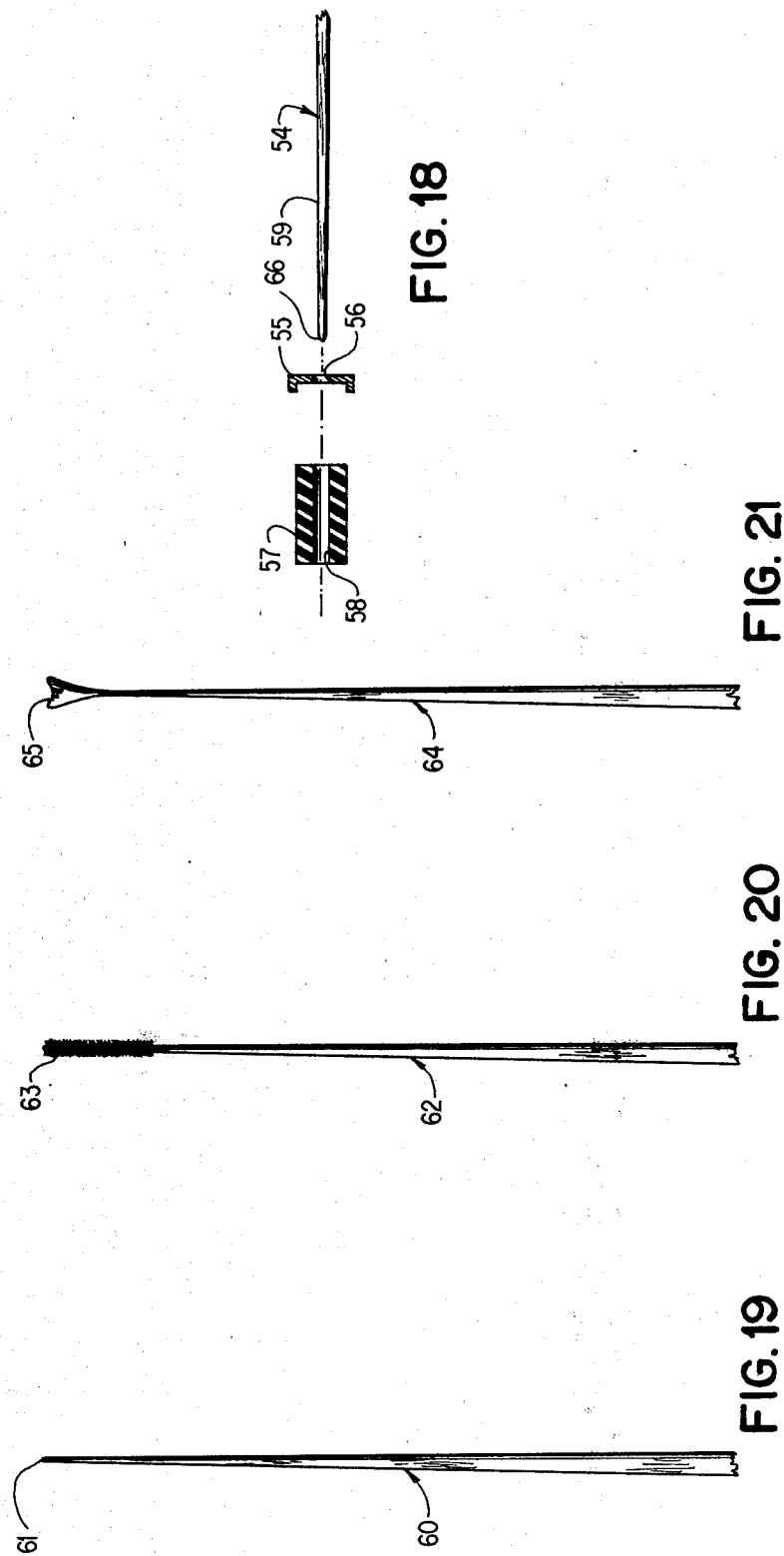

FLEXIBLE TEETH-CLEANING DEVICE

This invention relates to a dental device and more particularly to a device which aids in picking or cleaning particles in the vicinity of the teeth.

The toothpick is still utilized as a means for cleaning particles from and around teeth. It can be difficult and awkward to manipulate the toothpick in the mouth. The present invention is a device which stabilizes the toothpick and on which a brushed end or any type configuration of end can be utilized on the shaft of the device.

An object of the present invention is to stabilize a teeth-cleaning device with respect to the teeth.

Another object of the present invention is to provide a teeth-cleaning device which cleans teeth and which may be moved in any desired cleaning motion, with the device remaining stabilized with respect to the teeth.

A further object of the present invention is to provide a teeth-cleaning device which may be stabilized with respect to the teeth and which may have a pick, brushed, or irregularly-shaped end.

Still another object of the present invention is to provide a flexible positioning means for use in a teeth-cleaning device to stabilize the teeth-cleaning device.

Another object of the present invention is to have a flexible stabilizing means which comprises a guard face and flexible struts secured to a shaft.

A further object of the present invention is to have stabilizing means with a flexible guard to be positioned against the teeth, with a retainer secured to a shaft controlling the pressure of the flexible guard against the teeth.

Still another object of the present invention is to provide a teeth-cleaning device which may be stabilized against the teeth and which may be utilized at any desired angle with respect to the teeth.

Another object of the present invention is to provide a flexible guard and retainer which may be secured to an ordinary toothpick to form a teeth-cleaning device.

These and other objects and features of the invention will be apparent from the following description and appended claims.

Briefly, the invention is a device for use in cleaning teeth and adjacent areas. The device comprises a shaft, a flexible rest, and securing means. The shaft has a cleaning end. The flexible rest has an opening through which the shaft extends. The flexible rest is operative to be placed against the teeth and adjacent areas to stabilize the position of the device. The securing means is secured to the shaft and to the flexible rest. When the flexible rest is placed against the teeth and adjacent areas and the shaft is pressed forward, the flexible area reduces in length, allowing the cleaning end of the shaft to project through the flexible rest a distance dependent on the distance the shaft is pressed forward.

The flexible rest may comprise a plurality of flexible struts secured to the securing means and extending outward from the securing means at varying positions with respect to the shaft. The flexible struts extend outward and form the opening through which the shaft extends. A guard face, which may be placed against the teeth and adjacent areas, is connected to the flexible struts. The cleaning end of the shaft may be secured within the flexible rest, reducing the possibility of accidental injury caused by the cleaning end of the shaft.

The securing means may be a base secured around the shaft with the cleaning end. The plurality of flexible struts may extend outward in a circular pattern around the opening in the flexible rest. The guard face may be circular in shape. The flexible rest may be a flexible body with an opening extending from a first end of the flexible body to a second end of a flexible body, with the cleaning end extending from the second end of the flexible body. The flexible rest may further comprise a pressing retainer secured to the shaft by the securing means and secured to the first end of the flexible body. When the shaft is pressed forward, the pressing retainer presses against the flexible body, thereby reducing in length the flexible body and allowing the cleaning end of the shaft to project through the flexible body a distance depending on the distance the shaft is pressed forward. The flexible body may be cylindrically shaped.

The cleaning end may be a toothpick end. The cleaning end may be a brushed end. The cleaning end may be an irregularly-shaped end.

The shaft may be a toothpick, the securing means friction, and the flexible rest a slip-on pressing retaining and a slip-on flexible guard. The flexible struts may flex in a manner that the shaft with the cleaning end can approach the teeth and adjacent areas at varying angles. The flexible body may flex in a manner that the shaft with the cleaning end can approach the teeth and adjacent areas at varying angles.

The invention will be more fully understood from the following detailed description and appended claims when taken with the drawings in which:

FIG. 1 is a partial side elevational view of a human face 2 showing teeth-cleaning device 1 being utilized.

FIG. 2 is an elevational view of teeth-cleaning device 1.

FIG. 3 is a side elevational view of teeth-cleaning device 1 in position to clean a food particle 24 adjacent to tooth 14.

FIG. 4 is a side elevational view of teeth-cleaning device 1 pressed inward to remove the food particle 24 adjacent to tooth 14.

FIG. 5 is a side elevational view of the teeth-cleaning device 1 in position to clean areas around tooth 14 from different angles of approach to tooth 14.

FIG. 6 is a front elevational view of teeth-cleaning device 1 pressed against a plurality of teeth, including tooth 14.

FIG. 7 is an enlarged partial side elevational view of teeth-cleaning device 1 in a rest position.

FIG. 8 is a top sectional view of a plurality of teeth showing how the teeth-cleaning device 1 may be positioned against the plurality of teeth.

FIG. 9 is an elevational view of teeth-cleaning device 26.

FIG. 10 is a side elevational view of teeth-cleaning device 26 at rest in a position to clean in the area of tooth 34.

FIG. 11 is a side elevational view of teeth-cleaning device 26 pressed forward against a plurality of teeth, including tooth 34, illustrating the removal of food particle 31 from around tooth 34.

FIG. 12 is a side elevational view of teeth-cleaning device 26 illustrating the removal of food particle 31 around tooth 34 utilizing an approach from different angles.

FIG. 13 is a front elevational view of teeth-cleaning device 26 pressed against a plurality of teeth, teeth-cleaning device 26 cleaning the area between teeth 34 and 35.

FIG. 14 is an enlarged partial side elevational view of teeth-cleaning device 26 at a rest position with a partial cut-away view showing the pick 44 connected to toothpick shaft 27.

FIG. 15 is a top sectional view showing a plurality of teeth illustrating how teeth-cleaning device 26 may be positioned against a plurality of teeth.

FIG. 16 is a partial side elevational view of teeth-cleaning device 26 pressed against a braced tooth 50, with brace sections 46, 47, 48, and 49 shown in section.

FIG. 17 is a partial side elevational view of teeth-cleaning device 26 in a depressed position forcing a brushed end 53 through teeth-cleaning device 26 to clean the area next to the braced tooth 50.

FIG. 18 is an exploded partial sectional view of a slip-on type flexible guard 57, with a slip-on retainer 55 utilized on an existing toothpick 54.

FIG. 19 is a partial enlarged view of standard toothpick 60 with a pick 61, which may be utilized in the present invention.

FIG. 20 is a partial enlarged view of a toothpick 62 with a brushed tip 63 which may be utilized in the present invention.

FIG. 21 is a partial enlarged view of a toothpick 64 with a spread end or flattened portion 65 which may be utilized in the present invention.

Referring now to the drawings, FIG. 1 is a partial side elevational view of a human face 2 showing teeth-cleaning device 1 being utilized. Human face 2 has a mouth with a plurality of teeth 3. Human hand 4 holds the end of the teeth-cleaning device 1. The teeth-cleaning device 1 is pressed against some of the plurality of teeth 3.

FIG. 2 is an elevational view of teeth-cleaning device 1. Teeth-cleaning device 1 comprises a toothpick shaft 5 and a flexible device, including guard face 6 and flexible guard struts 7, 8, 9, and 10. The flexible device is secured to the toothpick shaft 5 by attachment means 11. The attachment means 11 may be a base which is secured around toothpick shaft 5. The actual securing means to the base may be friction, or glue, or any other desired securing means. The toothpick shaft 5 has an end which may be pick 12.

FIG. 3 is a side elevational view of teeth-cleaning device 1 in position to clean a food particle 24 adjacent to tooth 14. Food particle 24 is an example of a food particle which might be located within the teeth after eating and which can be easily removed by the teeth-cleaning device 1. The guard face 6 is positioned against the tooth 14 and adjacent teeth to remove food particles located between, on, or around the teeth.

FIG. 4 is a side elevational view of teeth-cleaning device 1 pressed inward to remove the food particle 24 adjacent to tooth 14. When teeth-cleaning device 1 is pressed forward, the guard face 6 is firmly pressed against one or more teeth. The flexible guard struts 7, 8, 9, and 10 flex in order for the pick 12 to extend forward through the guard face 6 to aid in removing the food particle 24. The food particle may be located between the teeth, on the teeth, or anywhere around the teeth. Tooth 14 is shown extending from gum 25.

FIG. 5 is a side elevational view of the teeth-cleaning device 1 in position to clean areas around tooth 14 from different angles of approach to tooth 14. FIG. 5 shows the teeth-cleaning device 1 at two different angles. However, the teeth-cleaning device 1 may approach the teeth at virtually any angle. The flexible guard struts 7, 8, 9, and 10 will flex in any desired direction necessary to enable the pick 12 to extend through the guard face 6 and to the desired area for removal of the food particle 24.

FIG. 6 is a front elevational view of teeth-cleaning device 1 pressed against a plurality of teeth, including tooth 14. In FIG. 6, the teeth-cleaning device 1 is pressed against the tooth 14 and tooth 15 and the gum 25. The area being cleaned is between tooth 14 and tooth 15. The teeth shown are teeth 13, 14, 15, 16, and a portion of the tooth next to tooth 13. Once the guard face 6 is pressed against the plurality of teeth, the movement of the pick 12 may be controlled from the end of the toothpick shaft 5. The food particle may be loosened and removed by any type of motion desired by the user.

FIG. 7 is an enlarged partial side elevational view of teeth-cleaning device 1 in a rest position. In the rest position, the pick 12 may be located slightly behind the guard face 6. Therefore, the pick 12 would not extend outward from the guard face 6 and would be safer than the ordinary toothpick, less likely to stab, jab, or penetrate unwanted areas. However, the same design of teeth-cleaning device 1 may be utilized, with the pick 12 shorter than, the same distance as, or extending from the guard face 6 at the end of teeth-cleaning device 1.

FIG. 8 is a top sectional view of a plurality of teeth showing how the teeth-cleaning device 1 may be positioned against the plurality of teeth. The pick 12 is located in a manner so that particles may be removed between the teeth and from the front of the teeth, if the teeth-cleaning device 1 is properly located. In FIG. 8, the teeth-cleaning device 1 is positioned to remove particles from space 18 between teeth 14 and 15. The teeth-cleaning device 1 may remove particles from any of the teeth 13, 14, 15, and 16, or from any of the spaces 17, 18, and 19 between the teeth, or from the face of the teeth; namely face 20 of tooth 13, face 21 of tooth 14, face 22 of tooth 15, and face 23 of tooth 16. The device is designed so that with the flexible guard struts 7, 8, 9, and 10, the pick 12 may be extended forward any desired length in order to reach the appropriate particle for removal. With the guard face 6 firmly against the plurality of teeth, movement of the toothpick shaft 5 will result in a cleaning movement of pick 12 in order to produce whatever movement is necessary or desired for removal of particles.

FIG. 9 is an elevational view of teeth-cleaning device 26. Teeth-cleaning device 26 has a toothpick shaft 27, a flexible guard 29, and a retainer 28. Flexible guard 29 has a face 30 which may be made of a material which is soft and flexible and will not damage teeth or braces and which may be the same material of which the entire flexible guard 29 is composed.

FIG. 10 is a side elevational view of teeth-cleaning device 26 at rest in a position to clean in the area of tooth 34. At rest, the pick 44 at the end of toothpick shart 27 is shown within the confines of flexible guard 29. Utilizing the principles of this invention, the pick 44 may be within the confines of flexible guard 29, the same distance as the outer portion of flexible guard 29, or may extend from the flexible guard 29. However, for safety purposes, it is advisable that the pick 44 be within the confines of flexible guard 29.

FIG. 11 is a side elevational view of teeth-cleaning device 26 pressed forward against a plurality of teeth, including tooth 34, illustrating the removal of food particle 31 from around tooth 34. In FIG. 11, the toothpick shaft 27 has been pressed forward. The retainer 28 presses against the flexible guard 29. The flexible guard 29 presses firmly against a plurality of teeth or gum areas. The pick 44, thereby, extends through the flexible guard 29 and aids in removing the food particle 31 from adjacent to tooth 34 extending from gum 32.

FIG. 12 is a side elevational view of teeth-cleaning device 26 illustrating the removal of food particle 31 around tooth 34 utilizing an approach from different angles. The teeth-cleaning device 26 is designed to be effective no matter what the angle of approach of toothpick shaft 27 with relationship to the teeth or food particles which are to be removed. FIG. 12 illustrates two angles of approach, one in broken lines, illustrating how the pick 44 may be extended to a desired area from two varying angles. Any angle may be utilized with the present invention.

FIG. 13 is a front elevational view of teeth-cleaning device 26 pressed against a plurality of teeth, teeth-cleaning device 26 cleaning the area between teeth 34 and 35. Teeth-cleaning device 26 may be of any desired diameter or shape which performs the function of the present invention. The retainer 28 may be of any desired shape or size which performs the function of the present invention. Teeth-cleaning device 26 may be moved along the teeth to remove any particles on the teeth, between the teeth, or near the teeth.

FIG. 14 is an enlarged partial side elevational view of teeth-cleaning device 26 at a rest position with a partial cutaway view showing the pick 44 connected to toothpick shaft 27. FIG. 14 shows the toothpick shaft 27 with a retainer 28 secured to toothpick shaft 27. Flexible guard 29 is secured to the retainer 28. Flexible guard 29 has an opening 45 through it, through which the toothpick shaft 27 extends. The pick 44, which is the end of toothpick shaft 27, extends from the flexible guard 29 when the toothpick shaft 27 is pressed forward. The pressing retainer 28 may be secured to the toothpick shaft 27 by friction, glue, or any other securing means. The securing means is what holds the flexible device onto the toothpick shaft 27.

FIG. 15 is a top sectional view showing a plurality of teeth illustrating how teeth-cleaning device 26 may be positioned against a plurality of teeth. FIG. 15 shows the flexible guard 29 positioned against teeth 34 and 35 in order to clean or remove particles in space 38 between teeth 34 and 35. By re-positioning the teeth-cleaning device 26 by movement of the toothpick shaft 27, teeth-cleaning device 26 may be positioned at any desired position against the plurality of teeth or gum areas in order to clean or remove particles from on the teeth, between the teeth, or around the teeth. The teeth-cleaning device 26 is designed so that it may also remove any particles from the face of each tooth; i.e. face 40 of tooth 33, face 41 of tooth 34, face 42 of tooth 35, and face 43 of tooth 36. The teeth-cleaning device 26 may also remove particles from the spaces between the teeth; namely space 37 between teeth 33 and 34, space 38 between teeth 34 and 35, and space 39 between teeth 35 and 36.

FIG. 16 is a partial side elevational view of teeth-cleaning device 26 pressed against a braced tooth 50, with brace sections 46, 47, 48, and 49 shown in section. FIG. 16 is illustrative to show that the teeth-cleaning device 26, as well as the teeth-cleaning device 1, may be utilized to clean areas even when braces are on the teeth. The face 30 of flexible guard 29 is of a soft, flexible material which is designed not to damage the teeth or braces. The guard face 6 of teeth-cleaning device 1 is formed of material which will not damage the teeth or braces. Teeth-cleaning device 1 or teeth-cleaning device 26 may be positioned to remove particle in specific areas without endangering the teeth, gums, or braces, if there are braces on the teeth. Tooth 50 is shown having a brace comprising sectionalizing pieces 46, 47, 48, and 49. Tooth 50 extends from gum 51. The teeth-cleaning device 26 is positioned so that those brace sections will not be damaged.

FIG. 17 is a partial side elevational view of teeth-cleaning device 26 in a depressed position forcing a brushed end 53 through teeth-cleaning device 26 to clean the area next to the braced tooth 50. In FIG. 17, a brush end 53 is shown secured to the end of toothpick shaft 27. Toothpick shaft 27 may have an end which is a brush, or pick, or any type of shaped object. The opening in flexible guard 29 is such that whatever the end piece desired for toothpick shaft 27, it will comfortably move within flexible guard 29. FIG. 17 shows a braced tooth 50 with brace sections 46, 47, 48, and 49. The teeth-cleaning device 26 pressed in for utilization does not injure the teeth, gums, or braces.

FIG. 18 is an exploded partial sectional view of a slip-on type flexible guard 57, with a slip-on retainer 55 utilized on an existing toothpick 54. The teeth-cleaning device 26 may be formed by a slip-on retainer 55, with an opening 56, which can be pressed onto a sloped toothpick 54 with a flexible guard 57, with an opening 58, pressed onto the slip-on retainer 55. The opening 56 in slip-on retainer 55 would be designed to be of such a diameter that the retainer will be secured at the proper position onto the existing toothpick 54. Existing toothpick 54 has a tapered portion 59 which will extend through the opening 56 in slip-on retainer 55. The tapered portion 59 will continue through opening 58 in flexible guard 57. Pick 66 on the end of existing toothpick 54 will extend through flexible guard 57, when being utilized in a similar manner that pick 55 extends through flexible guard 29.

FIG. 19 is a partial enlarged view of standard toothpick 60 with a pick 61, which may be utilized in the present invention.

FIG. 20 is an partial enlarged view of a toothpick 62 with a brushed tip 63 which may be utilized in the present invention.

FIG. 21 is a partial enlarged view of a toothpick 64 with a spread end or flattened portion 65 which may be utilized in the present invention.

The present invention will stabilize a teeth-cleaning device with respect to the teeth. With the device remaining stabilized, a teeth-cleaning device which cleans teeth, may be moved in any desired cleaning motion. A flexible positioning means is used in a teeth-cleaning device to stabilize the device. The device may be stabilized against the teeth and may be utilized at any desired angle with respect to the teeth. The present invention has a flexible stabilizing means which comprises a guard face and flexible struts secured to a shaft. The present invention has a stabilizing means with a flexible guard to be positioned against the teeth, with a retainer secured to a shaft controlling the pressure of the flexible guard against the teeth. The flexible guard and retainer may be secured to an ordinary toothpick to form a teeth-cleaning device. The present invention, which cleans teeth, may have a pick, brushed, or irregularly-shaped end.

The present invention basically improves the toothpick or toothbrush in a way that the present teeth-cleaning devices may be packaged to be disposable or could be re-usable. The device may have a thickness or diameter so that the tip, whether a pick, brush, or other shaped end, can fit up into and between normal teeth. The present invention enables the teeth-cleaning device to be stabilized against the teeth to prevent injury to the teeth or gum areas. Normal toothpicks, without the control designed into the present invention, can be utilized to cause injury, dislodge fillings, break off because of lack of control, and generally to be detrimental to the user. The present invention provides control to the user. With a normal toothpick, in order to provide certain movements of the toothpick with a degree of control, the fingers of the hand of the user have to virtually be within the mouth areas. With the present invention, the fingers of the hand can be away from the mouth areas, providing a more hygienic, tasteful method and device of removing foreign material from the teeth area.

A pressing surface presses against the teeth area in order to provide control for the moving shaft which has the pick, brush, or irregularly-shaped end. The flexible rest may have a special pressing material secured to it to press against the teeth and adjacent areas.

The teeth-cleaning device provides support and is a guide means for the shaft being utilized to clean or brush the teeth area.

In essence, the flexible device can be a guard face with flexible struts, such as guard face 6 and flexible struts 7, 8, 9, and 10, or can be like flexible guard 29 composed of material which is flexible. The flexible device is secured to the shaft and can be made out of any exterior material which will not damage braces, teeth, or the gum areas. The flexible device has an open area through which the shaft with the desired end extends. The opening does not have to be round, but can be of any size or shape. The opening does not have to be totally around the shaft, but could be partially around the shaft. The flexible device may be of any shape or size and composed of any material which will not damage the teeth, braces, or gum areas.

While the invention has been described with reference to specific embodiments, the description is illustrative and is not to be construed as limiting the scope of the invention. Various modifications and changes may occur to those skilled in the art without departing from the spirit and scope of the invention as defined by the appended claims.

I claim:
1. A device for use in cleaning teeth and adjacent areas comprising:
   a. a shaft with a cleaning end;
   b. a flexible rest, with an opening through which said shaft extends, operative to be placed against said teeth and adjacent areas to stabilize the position of said device and flexible rest comprising a plurality of flexible struts secured to said securing means and extending outward from said securing means at varying positions with respect to said shaft, forming said opening through which said shaft extends, and a guard face, which may be placed against said teeth and adjacent areas, and to which each of said flexible struts are secured; and
   c. securing means secured to said shaft with a cleaning end, and to said flexible rest,
   whereby when said flexible rest is placed against said teeth and adjacent areas and said shaft is pressed forward, said flexible area reduces in length allowing said cleaning end of said shaft to project through said flexible rest a distance dependent on the distance said shaft is pressed forward.

2. A device according to claim 1 wherein, at rest, said cleaning end of said shaft is secured within said flexible rest reducing the possibility of accidental injury caused by said cleaning end of said shaft.

3. A device according to claim 1 wherein said cleaning end is a toothpick end.

4. A device according to claim 1 wherein said cleaning end is a brushed end.

5. A device according to claim 1 wherein said cleaning end is a concavedly-shaped end.

6. A device according to claim 1 wherein said flexible struts flex in a manner that said shaft with said cleaning end can approach said teeth and adjacent areas at varying angles.

7. A device according to claim 1 wherein said flexible rest further comprises attachment means comprising a base secured around said shaft with said cleaning end, with said plurality of flexible struts extending outward in a circular pattern around said opening in said flexible rest.

8. A device according to claim 7 wherein said guard face is circular in shape.

* * * * *